(12) United States Patent
Eriksson et al.

(10) Patent No.: US 8,632,523 B2
(45) Date of Patent: Jan. 21, 2014

(54) WOUND TREATMENT DEVICE EMPLOYING NEGATIVE PRESSURE

(75) Inventors: Elof Eriksson, Wellesley Hills, MA (US); W. Robert Allison, Sudbury, MA (US); Christian Baker, Weymouth, MA (US)

(73) Assignee: Applied Tissue Technologies, LLC, Wellesley Hills, MA (US)

( * ) Notice: Subject to any disclaimer, the term of this patent is extended or adjusted under 35 U.S.C. 154(b) by 218 days.

(21) Appl. No.: 12/601,394

(22) PCT Filed: May 27, 2008

(86) PCT No.: PCT/US2008/064897
§ 371 (c)(1),
(2), (4) Date: Sep. 20, 2010

(87) PCT Pub. No.: WO2008/154158
PCT Pub. Date: Dec. 18, 2008

(65) Prior Publication Data
US 2011/0004168 A1    Jan. 6, 2011

Related U.S. Application Data

(60) Provisional application No. 60/931,599, filed on May 24, 2007.

(51) Int. Cl.
*A61M 1/00* (2006.01)
(52) U.S. Cl.
USPC .......................................... 604/543; 604/317
(58) Field of Classification Search
USPC .................................................. 604/317, 543
See application file for complete search history.

(56) References Cited

U.S. PATENT DOCUMENTS

| 2,283,089 A | 5/1942 | Pfauser |
| 5,034,006 A * | 7/1991 | Hosoda et al. ................ 604/317 |
| 5,312,385 A | 5/1994 | Greco |
| 5,437,602 A | 8/1995 | Polyakov et al. |
| 5,437,651 A * | 8/1995 | Todd et al. .................... 604/313 |
| 5,447,504 A | 9/1995 | Baker et al. |

(Continued)

FOREIGN PATENT DOCUMENTS

| GB | 2378392 A | 12/2003 |
| JP | 51-22888 | 2/1976 |

OTHER PUBLICATIONS

International Search Report and Written Opinion for Int'l Application No. PCT/US06/25391, Feb. 2, 2007.

(Continued)

*Primary Examiner* — Philip R Wiest
*Assistant Examiner* — Benjamin Klein
(74) *Attorney, Agent, or Firm* — Quarles & Brady LLP (57) ABSTRACT

The present invention provides a device for wound treatment, comprising a chamber that includes an inner surface and defines a treatment space, the chamber being made of a flexible, impermeable material. The device further includes a plurality of structures configured to exert mechanical stress on a wound, the plurality of structures intruding from the inner surface of the chamber into the treatment space. The device further includes a tube having a first end connected to the chamber, the tube being in fluid communication with the treatment space so as to enable at least one selected from the group of applying negative pressure to the treatment space and applying a therapeutic modality.

49 Claims, 9 Drawing Sheets

(56) References Cited

U.S. PATENT DOCUMENTS

| | | | |
|---|---|---|---|
| 5,527,265 | A | 6/1996 | McKeel |
| 5,720,713 | A | 2/1998 | Hutchison |
| 5,807,290 | A | 9/1998 | Barry |
| 6,053,882 | A | 4/2000 | Johansen |
| 6,290,685 | B1 * | 9/2001 | Insley et al. ............ 604/317 |
| 6,566,577 | B1 | 5/2003 | Addison et al. |
| 6,652,484 | B1 * | 11/2003 | Hunckler et al. ......... 604/74 |
| 6,855,135 | B2 | 2/2005 | Lockwood et al. |
| 7,128,735 | B2 | 10/2006 | Weston |
| 7,216,651 | B2 | 5/2007 | Argenta et al. |
| 7,867,206 | B2 * | 1/2011 | Lockwood et al. ........ 604/313 |
| 7,884,258 | B2 | 2/2011 | Boehringer et al. |
| 2002/0198503 | A1 | 12/2002 | Risk, Jr. |
| 2004/0064132 | A1 * | 4/2004 | Boehringer et al. ........ 604/543 |
| 2005/0004534 | A1 * | 1/2005 | Lockwood et al. ......... 604/304 |
| 2005/0137539 | A1 | 6/2005 | Biggie et al. |
| 2005/0267424 | A1 | 12/2005 | Eriksson et al. |
| 2008/0108977 | A1 * | 5/2008 | Heaton et al. ............. 604/543 |
| 2009/0312723 | A1 | 12/2009 | Blott et al. |

OTHER PUBLICATIONS

International Search Report and Written Opinion for Int'l Application No. PCT/US08/64897, Aug. 29, 2008.

U.S. Appl. No. 60/819,146, filed Jul. 7, 2006.

* cited by examiner

WOUND TREATMENT DEVICE EMPLOYING NEGATIVE PRESSURE

CROSS REFERENCE TO RELATED APPLICATIONS

This application represents the national stage application of International Application PCT/US2008/064897 filed 27 May 2008, which claims the benefit of U.S. provisional Patent Application No. 60/931,599, filed 24 May 2007, which are incorporated herein by reference in their entirety for all purposes.

STATEMENT REGARDING FEDERALLY SPONSORED RESEARCH OR DEVELOPMENT

Not applicable.

FIELD OF THE INVENTION

The invention relates generally to the field of wound treatment, and more particularly, to a device for treating wounds with negative pressure and/or therapeutic modalities.

BACKGROUND OF THE INVENTION

Many wounds can be treated by the application of negative pressure. The method of such treatment has been practiced for many years. The benefits of such treatment can include: reduction of edema; reduction of wound exudate; reduction of wound size; and stimulation of formation of granulation tissue. Existing devices and appliances for the provision of negative pressure wound therapy are complex. Such devices typically encompass a porous insert such as foam or gauze that is placed into the wound; a tube connecting the insert to a source of suction; a flexible cover draped over these components and sealed to the skin around the wound; an electrically powered suction pump; controls to operate the pump and monitor the system; containers to collect wound fluids; filters to process the materials removed from the wound; and safety systems to prevent harm to the patient and to block the escape of biological materials into the outside environment. These devices are expensive, labor intensive, and restrictive of patient mobility. The many components, particularly the seals around the insert and the tube, tend to leak. Therefore, suction must be applied either continuously or frequently.

Continuous suction is typically achieved by a vacuum pump powered by an electric motor. These systems require complex means to measure, monitor, and control the operation of the pump in order to ensure the safety of the patient. In addition, many negative pressure devices are contraindicated in the presence of necrotic tissue, invasive infection, active bleeding, and exposed blood vessels. They require the use of a porous insert (i.e., a sponge, foam, gauze, mesh, etc.) in the wound. The insert may present two problems: growth of tissue into the insert, and the harboring of infectious and/or undesirable materials in the insert. Wound tissue can grow into and around such inserts, causing adverse results to the healing process. Moreover, such inserts can retain wound fluid and microorganisms, and can therefore become contaminated and/or infected, presenting an adverse effect to the healing process. In addition, the high cost of these devices may deter or delay their use on patients.

Existing negative pressure treatment devices are labor intensive since they require the user to assemble, fit and customize a number of components. First, the user must prepare, trim, and size a porous insert of foam, gauze, mesh, or other material that will be placed in the wound. Next, the user must position a tube in the insert, and then cover the tube and insert with a material that is intended to create a leakproof seal. In practice, and as mentioned above, such compositions tend to leak, requiring the frequent application of suction in order to establish and re-establish negative pressure within the space about the wound. In addition, currently available negative pressure devices and systems block the view of the wound, making monitoring and diagnosis more difficult. Therefore, an improved device for applying negative pressure to wounds is needed.

BRIEF SUMMARY OF THE INVENTION

In a first aspect, the present invention is summarized as a device for wound treatment, comprising a chamber that includes an inner surface and defines a treatment space, the chamber being made of a flexible, impermeable material. The device further includes a plurality of structures configured to exert mechanical stress on a wound and configured to create pathways through which negative pressure can be distributed and maintained in the treatment space, the plurality of structures intruding from the inner surface of the chamber into the treatment space. The device further includes a tube having a first end connected to the chamber, the tube being in fluid communication with the treatment space so as to enable at least one selected from the group of applying negative pressure to the treatment space and applying a therapeutic modality.

In some embodiments, the plurality of structures and the chamber are part of a single ply of material. In addition, in some embodiments, each of the structures in the plurality of structures is semi-rigid.

In some embodiments, the device includes a wedge-shaped manual pump, and the treatment space is in fluid communication with the wedge-shaped manual pump. The wedge-shaped manual pump may include a spring that biases the wedge-shaped manual pump to an uncompressed position.

In a second aspect, the present invention is as a method of treating a wound that includes evenly applying negative pressure across the wound with any of the devices described herein.

The foregoing and other objects and advantages of the invention will appear in the detailed description that follows. In the description, reference is made to the accompanying drawings that illustrate a preferred embodiment of the invention.

BRIEF DESCRIPTION OF THE DRAWINGS

The invention may be understood by reference to the following description taken in conjunction with the accompanying figures, in which like reference numerals identify like elements. It should be understood that figures represent an example of the present invention and components are not necessarily shown to be proportional to one another. The terms "chamber wall" or "wall" mean any part of the chamber device that forms or encloses the chamber treatment space. The term "overview" means a view from the inside of the chamber treatment space looking toward the interior surface of the chamber wall.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF PREFERRED EMBODIMENTS

While the present invention may be embodied in any of several different forms, the present invention is described herewith the understanding that the present disclosure is to be considered as setting forth an exemplification of the present invention that is not intended to limit the invention to the specific embodiment(s) illustrated.

The present invention is directed to providing a simple, safe, disposable, and cost-effective device that is easy to install and operate, that allows freedom of motion to the patient, and that overcomes, or at least reduces the effects of, one or more of the problems set forth above. The present invention does not require the use of a porous insert. The one-piece construction of the device eliminates virtually all leaks, therefore preserving and maintaining negative pressure within the wound without the need for constant or frequent regeneration of negative pressure. In addition, the structure of the device is configured to promote wound healing and to create pathways through which negative pressure can be distributed and maintained in the treatment space. The indications for the present invention may be expanded beyond the limitations imposed on current devices. The cost-effectiveness of the present invention may lead to the provision of negative pressure wound therapy on a more widespread basis and earlier in the timeline of wound care.

One aspect of the present invention is seen in a wound treatment device including a chamber defining a treatment space around the wound. The flexible adhesive base of the chamber forms a water-tight and gas-tight seal. A tube communicates from the treatment space to a source of suction. The suction source also serves as a receptacle for materials removed from the chamber. All components preferably are inexpensive, lightweight, and disposable.

Figure 1:
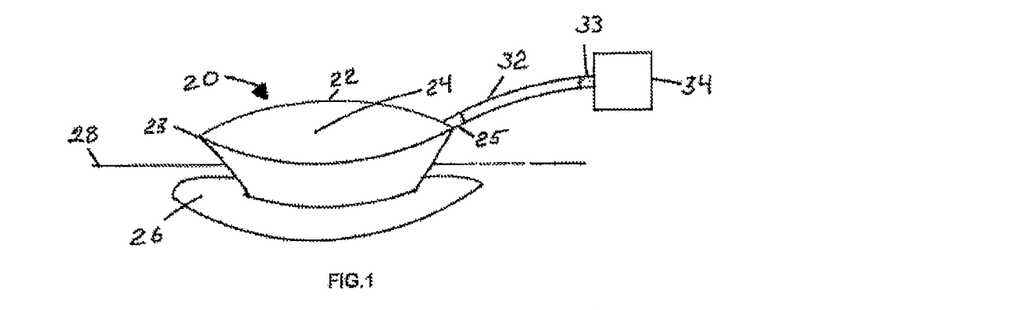
FIG. 1 is a perspective view of a wound chamber treatment device with a tube leading from a chamber to a suction source.
Figure 2:
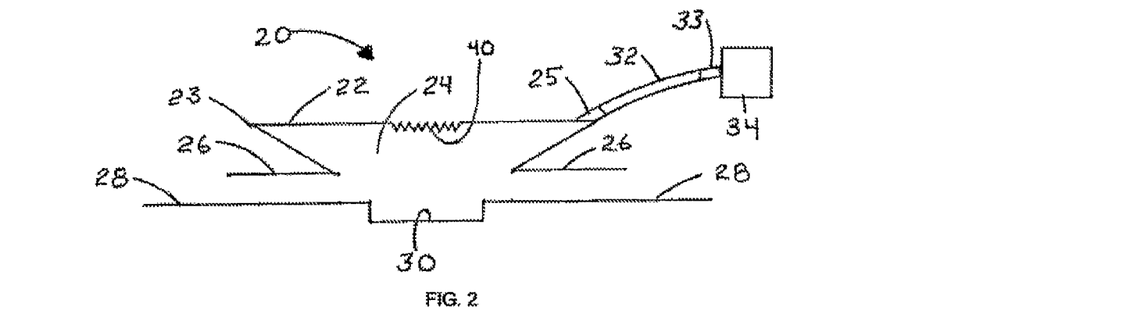
FIG. 2 is a side sectional view of the device in FIG. 1.
Figure 19:
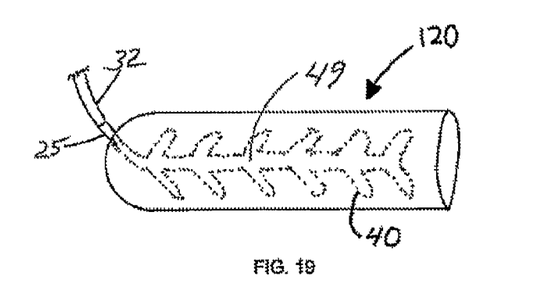
FIG. 19 is a view of a wound chamber configured as a tube for placement over a limb, and having engineered structures and channels on the interior surface of the chamber wall.

Referring first to FIGS. 1 and 2, views of a wound treatment device 20 are provided. The device 20 includes a chamber 22 defining a treatment space 24 and a base 26 that may be sealed to a skin surface 28 of a patient over a wound 30. In the illustrated embodiment, the chamber 22 has a bellows configuration with a fold 23. However, the invention is not so limited, and other configurations of a chamber formed of a flexible, moisture and gas impermeable material may be used. Materials from which the device 20 may be made will be discussed in further detail below. The device 20 can be designed for use with any wound or body part, using circular, square, rectangular, tubular, pouch, envelope or other shapes. For example, a chamber in the form of a tube or sleeve for placement over a limb is shown in FIG. 19. Referring again to FIGS. 1 and 2, a dermal or cutaneous adhesive material may be provided on a bottom surface of the base 26 for providing a fluid-tight seal with sufficient adhesive strength to prevent inadvertent removal of the chamber 22 or breach of the fluid-tight seal during normal patient movement. Numerous adhesive materials sufficient for these purposes are known to those of ordinary skill in the art.

A tube 32 is attached to the chamber 22 preferably at a location spaced above the base 26 and communicates with the treatment space 24. The tube 32 is constructed to maintain its shape without collapsing and to permit the passage of wound fluids and wound debris. The tube 32 may be permanently fixed to the chamber 22, or a fitting 25 may be provided to allow the attachment and removal of the tube 32 or any other device that can deliver material or therapies to, or remove material from, the treatment space 24. The tube 32 may terminate at a wall of the chamber 22, or it may extend through the wall a distance and terminate within the treatment space 24, where it may communicate with such space, with channels formed on the inner surface of the chamber wall, or with folds formed in the chamber wall. As another alternative, the tube 32 may connect to the chamber 22 with a Luer fitting. The tube 32 is sealed to the chamber 22 in such a manner as to prevent the escape of liquid or gas from the treatment space 24 to the outside environment. A distal end of the tube 32 terminates at a suction device 34. The suction device 34 may be a pump, although other types of devices may be used as discussed below. A fitting 33 may be provided to permit the detachment and reattachment of a suction device 34 to the tube 32.

Figure 3:
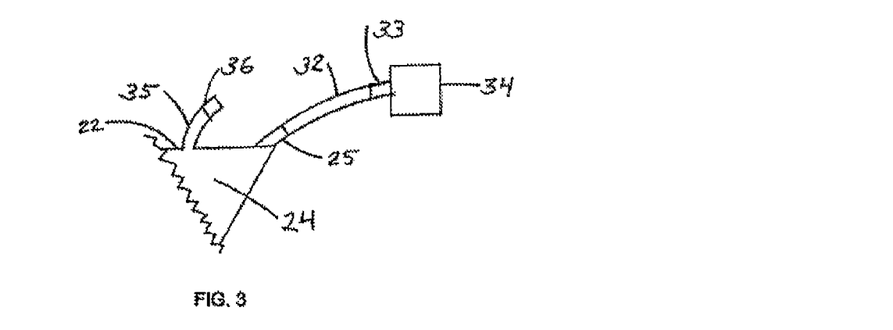
FIG. 3 is a sectional view of the device in FIG. 1 with an additional tube leading to a port.
Figure 4:
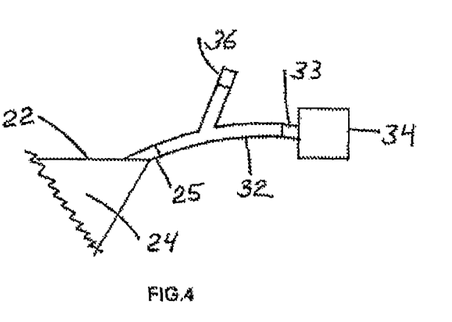
FIG. 4 is a sectional view of the device in FIG. 1 with a branching tube leading to a port.

Turning to FIG. 3, a sectional view of the device 20 is provided, showing a second tube 35 attached to the chamber 22 and communicating with the treatment space 24, with channels, or with folds. A distal end of the tube 35 terminates in a portal 36. The invention is not limited to any number of communicating tubes, and multiple tubes and portals may be provided for accessing the treatment space 24. FIG. 4 shows the device in FIG. 1 with a branch of the tube 32 that leads to a portal 36. The portal 36 may be used for the delivery of therapeutic modalities—such as antimicrobials, antibiotics, antifungals, and analgesics—prior to, during, or after the delivery of negative pressure. As such, the portal 36 may be a Luer fitting configured for attachment to a container or a syringe. Alternatively, therapeutic modalities may be delivered through the same tube 32 that communicates with the suction device 34.

Figure 5:
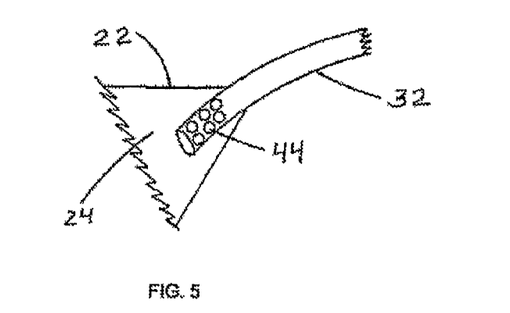
FIG. 5 is a perspective view of the end of the tube communicating with the interior chamber space.

Turning now to FIG. 5, the end of the tube 32 extending into the chamber space 24 is shown with multiple apertures 44. The purpose of the apertures 44 is to ensure that gases, liquids, wound fluid, debris, and other materials can flow and move out of the chamber space 24 into the tube 32 without impediment.

Figure 6:
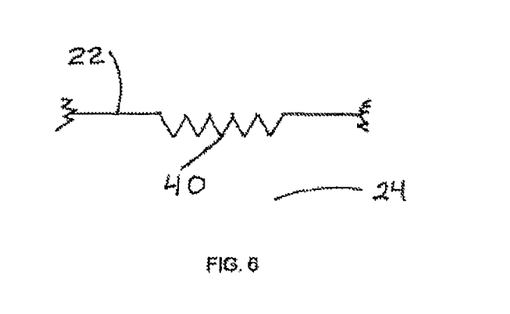
FIG. 6 is a side sectional view of structures engineered on and into the interior surface of the chamber wall, where the structures are of uniform size and shape, and are spaced uniformly apart.

Referring to FIG. 6, the interior surfaces of the chamber wall may be configured with structures 40 that are engineered on the surfaces. The portions of the interior surfaces with engineered structures 40 may be varied from that shown in the figures, and preferably a high percentage of the interior surfaces include engineered structures 40. The structures preferably cover at least 50% of the interior surfaces, and more preferably at least 95% of the interior surfaces. These structures are raised when viewed from within the chamber space 24, and they intrude into such space in directions generally perpendicular to the interior surfaces of the chamber space 24. These structures can be any shape, including without limitation a cone, a pyramid, a pentagon, a hexagon, a half sphere, a dome, a rod, an elongated ridge with rounded sides, or an elongated ridge with square sides. The structures can be provided as identical shapes, or in any combination of shapes. The structures can be provided with identical sizes, or in any combination of different sizes. The structures may be uniformly or non-uniformly spaced from each other. In addition, the structures may be separated by a portion of the surface of the chamber 22. The distance of intrusion into the chamber treatment space 24 from the chamber wall by such structures is preferably between 0.01 mm and 20 mm, and is more preferably between 1 mm and 1 cm. The spacing between such structures is preferably between 0.01 mm and 5 cm.

The engineered structures 40 interface with the wound surface during use of the device 20. One purpose of these structures is to ensure that negative pressure established within the chamber space 24 is evenly distributed and maintained throughout such space. As negative pressure is established within the tube that leads to the source of suction, the chamber will lie tighter against the wound tissue. The device 20 includes the engineered surfaces 40 in order to define pathways to establish, distribute, and maintain negative pressure across the wound surface and prevent complete contact between the inner surfaces of the chamber and the wound tissue. Without such structures, the chamber wall would make complete contact with the wound surface. As a result, there would be no space within which negative pressure could be established, distributed, and maintained. Therefore, the engineered structures are preferably semi-rigid. The term "semi-rigid" should be understood as meaning that deformation only occurs at a microscopic level under operating negative pressures in the range of 0.5-2 psi. Alternatively, the engineered structures may be somewhat flexible depending on the spacing between the structures. In addition, the structures are engineered to reduce the extent to which wound tissue can enter the space between the structures, so that a sufficient amount of open space is maintained.

An additional purpose of these structures is to serve as a form of stimulation to the wound to produce beneficial results, including without limitation the formation of granulation tissue and an increase of micromechanical forces. Such mechanical forces provide stimulation to a portion of the wound tissue, which has been suggested as a contributing factor to the effectiveness of negative pressure wound therapy. From the above discussion and the figures, it should be understood that the flexible chamber is movable over a range of positions. The range of positions includes a first position, such as the position shown in FIGS. 1 and 2, in which the engineered structures 40 are spaced apart from the opening of the chamber defined by the base 26. The range of positions also includes a second position in which at least some of the engineered structures 40 are positioned in the opening of the chamber. The second position is preferably a position in which the engineered structures 40 engage the wound.

The chamber wall can be formed of any appropriate medical grade material that has the following characteristics: flexibility, conformability, gas impermeability, liquid impermeability, the ability to be formed, tooled, and engineered, and the ability to retain the shape, function, and effectiveness of raised engineered structures under desired ranges of negative pressure. In addition, the material is preferably hypo-allergenic and provided to a medical facility in a sterile condition. For example, the chamber device may be made of a flexible, conformable material such as polyurethane, although other similar materials may also be used. The chamber is preferably designed to provide sufficient material to lie against the surface of the wound tissue without special sizing, trimming, or other customizing operations. The chamber may be made from a single ply of material, or may be constructed of multiple layers of material in and on which the structures are engineered. It should be understood that a single ply chamber may be made of multiple sheets of material during manufacturing, but is provided to a medical facility in a state in which the multiple sheets are bonded or otherwise connected to one another. For example, individual three dimensional shapes may be adhered or bonded to the inner surface of the chamber wall during manufacturing to provide the engineered structures. A single ply chamber could also be formed from a single sheet of material that defines both the chamber walls and the engineered structures. Alternatively, a multiple layer chamber is provided to a medical facility in a state in which layers of material are stacked to form the chamber. For example, the layer facing the interior treatment space of the chamber could be a layer containing engineered structures that is bonded onto a generally flat layer of material (or multiple sheets of generally flat layers) by a medical practitioner.

The engineered structures can be made by techniques familiar to those in the art, such as embossing, stamping, molding, forming, or bonding. If the structures are created by embossing their shape into the material, the embossed structures may be left in a concave state relative to the outside of the chamber as shown in FIG. 6. Embossed structures may also be formed on a single ply of material that also forms the walls of the chamber and the base. This may provide a chamber that is relatively flexible and semi-rigid structures on a single ply of material. Alternatively, the cavities may be filled with a suitable material to render the structures solid. As another alternative, solid structures can be affixed to the inner surfaces of the chamber.

Figure 7:
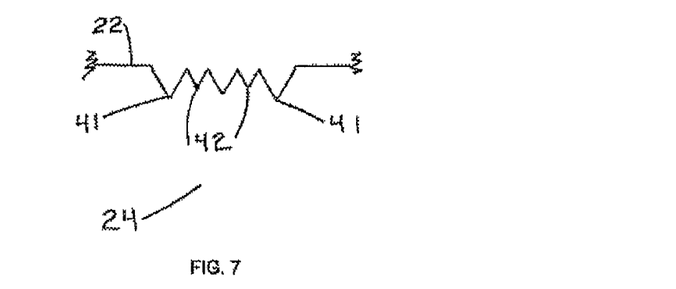
FIG. 7 is a side sectional view of two groups of structures engineered on and into the interior surface of the chamber wall, where one group intrudes into the chamber space, the other group intrudes to a lesser extent, and structures from these groups alternate in a regular pattern.
Figure 8:
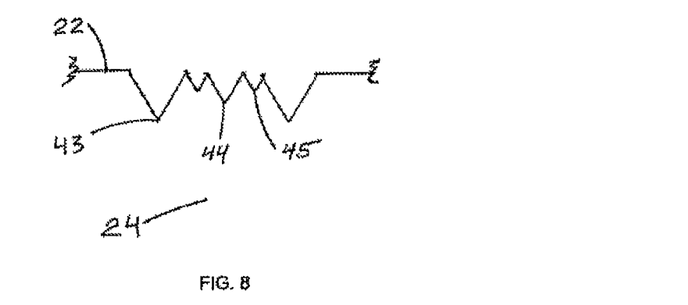
FIG. 8 is a side sectional view of three groups of structures engineered on and into the interior surface of the chamber wall, where such groups have varying degrees of intrusion into the chamber space and alternate in a regular pattern.
Figure 9A:
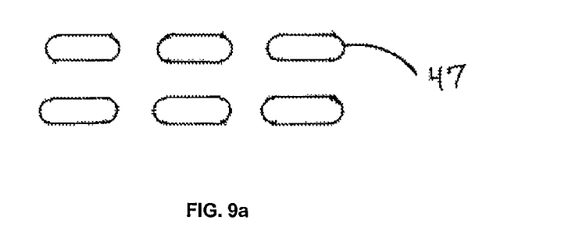
FIG. 9a is an overview of structures engineered on and into the interior surface of the chamber wall, where the structures consist of raised ridges.
Figure 9B:
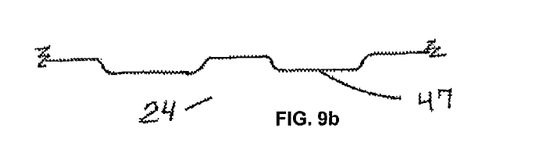
FIG. 9b is a side sectional view of the raised ridges of FIG. 9 with rounded edges.
Figure 9C:
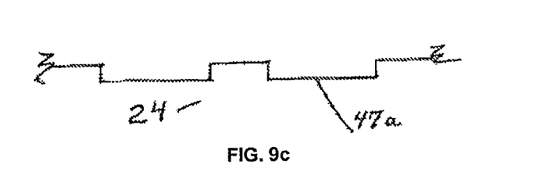
FIG. 9c is a side sectional view of the raised ridges of FIG. 9a with square cross sections.
Figure 10:
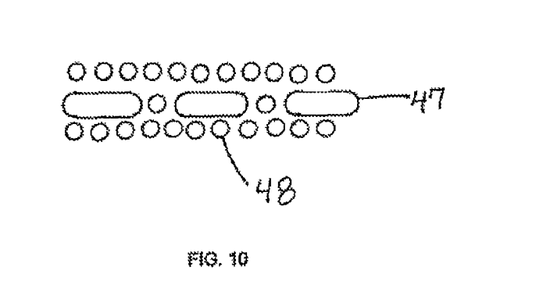
FIG. 10 is an overview of the raised ridge structures shown in FIG. 9, with the addition of raised dome structures positioned among the ridges.

The raised structures on the inner surfaces of the chamber wall can be configured and distributed in a number of patterns. For example, FIG. 6 is a side sectional view of a portion of a chamber wall, showing engineered structures 40 on the interior surface of the material that faces treatment space 24. Structures 40 are identical in shape and size, and are positioned uniformly apart from one another. As another example, FIG. 7 is a side sectional view showing engineered structures 41 and 42 intruding into the chamber space, where structures 41 intrude farther than structures 42, and the structures are configured in a regular alternating pattern of 41-42-41-42 and so forth. As yet another example, FIG. 8 is a side sectional view showing engineered structures 43, 44, and 45 intruding into the chamber space, where structures 43 intrude farther than structures 44 and 45, structures 44 intrude less than structures 43 but farther than structures 45, and structures 45 intrude less than structures 43 and 44. These structures are configured in a regular alternating pattern of 43-45-44-45-43-45-44-45-43 and so forth. The embodiment shown in FIG. 8 makes it difficult for soft wound tissue to penetrate all of the spaces among the raised structures. A sufficient amount of continuous space is established to make possible the distribution of negative pressure, as well as the addition of fluids and therapies and the removal of fluids and materials from the wound. As yet another example, FIG. 9a is an overview of a portion of the chamber wall, showing engineered structures 47 in the form of raised ridges. The engineered structures 47 may be rounded (FIG. 9b), square (FIG. 9c), or a combination thereof when viewed from the side. As yet another example, FIG. 10 is an overview showing engineered dome structures 48 interspersed with ridge structures 47. The engineered dome structures 48 are preferably semi-spherical when viewed from the side, although other shapes are contemplated.

Figure 11:
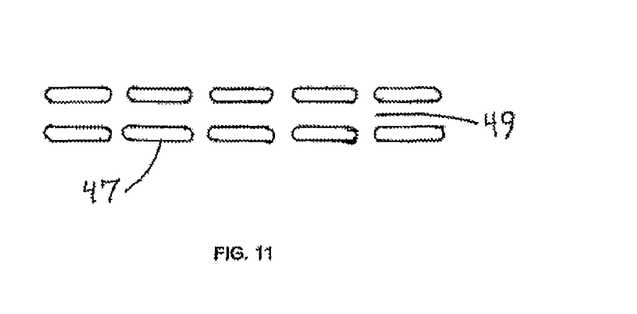
FIG. 11 is an overview of raised ridge structures engineered on and into the interior surface of the chamber wall, where two parallel lines of such structures form a channel.
Figure 12:
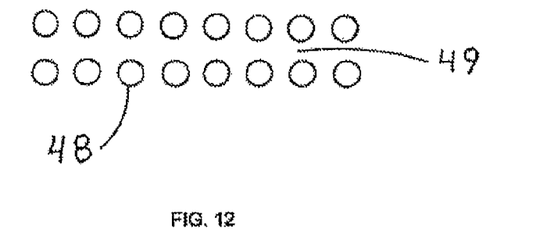
FIG. 12 is an overview of raised dome structures engineered on and into the interior surface of the chamber wall, where two parallel lines of such structures form a channel.
Figure 13:
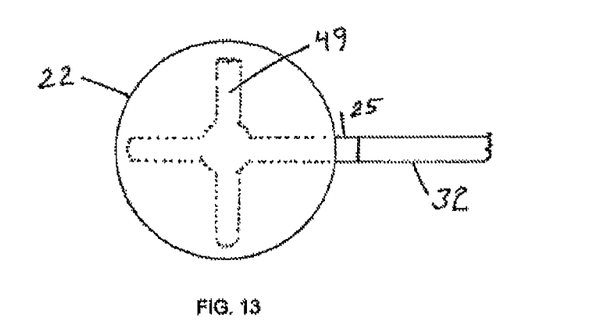
FIG. 13 is a view of a wound chamber, showing a pattern of channels leading to the center of the chamber and then to the tube communicating from the interior of the chamber space.
Figure 14:
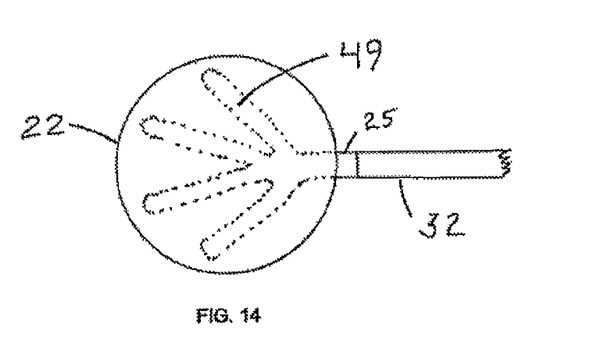
FIG. 14 is a view of a radiating pattern of channels leading to the communicating tube.
Figure 15:
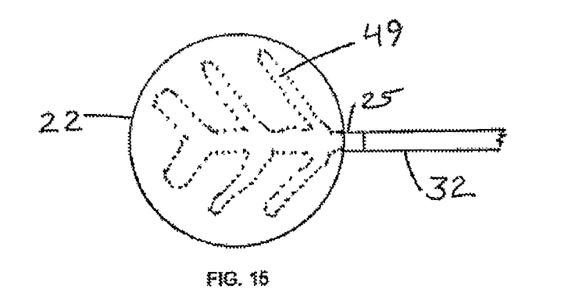
FIG. 15 is a view of a branching pattern of channels leading to the communicating tube.
Figure 16:
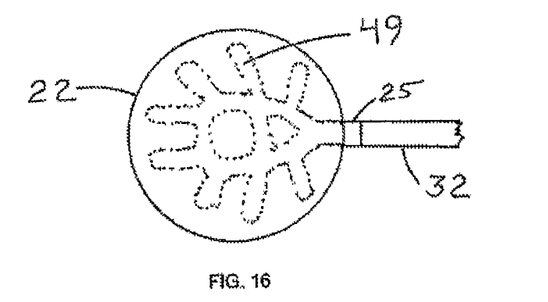
FIG. 16 is a view of a sub-branching pattern of channels leading to the communicating tube.

The distribution and maintenance of negative pressure within the chamber device and at all points on the wound may be enhanced by providing defined channel spaces as pathways among the raised engineered structures for the distribution of negative pressure. However, defined channel spaces are not required for providing fluid pathways within the treatment space. FIG. 11 is an overview of a portion of the chamber wall, showing structures 47 arranged in two parallel lines to form channel 49. FIG. 12 shows a channel 49 formed by two parallel lines of raised domed structures 48. Such channels can be configured in various patterns, such as radial, circular, concentric, or branching. FIGS. 13-16 show overviews of patterns of channels 49 leading from tube 32 along the interior surface of chamber 22 facing treatment space 24. For each pattern, the channel 49 defines a space that opens directly to the treatment space 24. The space preferably opens to the treatment space 24 over the entire length of the channel 49.

Figure 17:
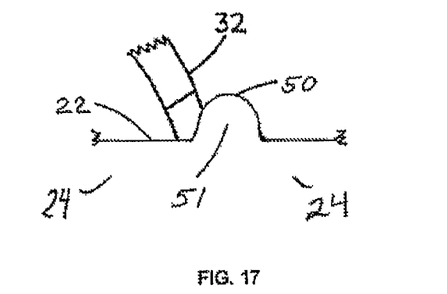
FIG. 17 is a side sectional view of a fold in the chamber wall.
Figure 18A:
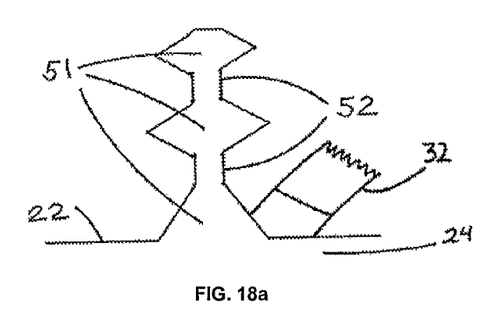
FIG. 18a is a side sectional view of a fold in the chamber wall, with structures engineered on and into the inner surface of the fold, which structures maintain continuous open space within the fold.
Figure 18B:
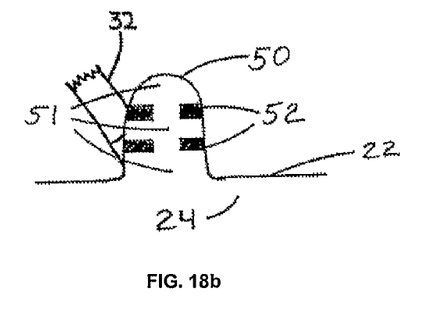
FIG. 18b is a side sectional view of the fold in the chamber wall of FIG. 17 with structures engineered on the inner surface of the fold.

The distribution and maintenance of negative pressure with the chamber device and at all points on the wound can also be enhanced by the use of folds in the chamber wall to create additional channel space for the distribution of negative pressure. When negative pressure is established within the chamber, the material will tend to fold along the pre-formed location. FIG. 17 shows a channel 50 formed in a fold of the chamber wall. The channel 50 defines a space that opens directly to the treatment space 24. The space preferably opens to the treatment space 24 over the entire length of the channel 50. In order to increase the amount of channel space within such fold, the walls of the fold can be configured with structures that prevent the collapse of such space, and ensure continuous open space for the distribution and maintenance of negative pressure, and the passage of liquid, gas, and other material. As an alternative, FIG. 18a shows engineered structures 52 that prevent the total collapse of the fold, and ensure continuous channel space 51. All channel spaces created on the interior surface of the chamber wall or by means of folds function as means to increase the effectiveness of distributing and maintaining negative pressure within the chamber, and also as means to enhance the effectiveness of removing gas, liquid, wound fluid, debris, and other materials from the chamber treatment space. As another alternative, FIG. 18b shows an embodiment similar to the embodiment shown in FIG. 17 with the addition of engineered raised structures 52 on opposite sides of the fold. The engineered structures 52 are provided so that the fold will not collapse to the point where all of its interior surfaces form a tight seal against the movement of negative pressure. However, some of the interior surfaces, such as those adjacent to the fold, preferably contact the wound to provide stimulation as discussed above. The folds described in the previous embodiments are preferably formed at certain defined areas by molding or embossing the surfaces of the chamber 22.

FIG. 19 shows a wound chamber device 120 for delivering negative pressure and therapeutic substances in the form of a tube that can be placed over a limb. The wound chamber device 120 is generally cylindrical and includes an open end and a closed end. The open end is preferably sealed with a cuff or collar (not shown), and the open end may include adhesive on the interior surface. The wound chamber device 120 includes engineered structures 40 and channels 49 on the interior surface of the chamber wall. The wound chamber device 120 may also include folds and channels as described above.

Figure 20:
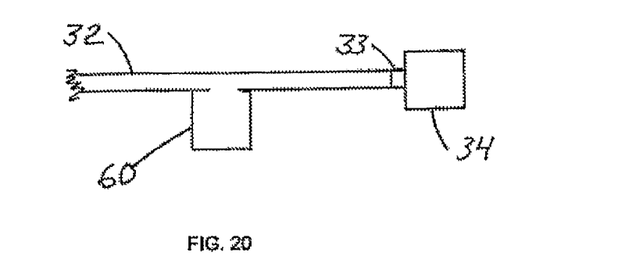
FIG. 20 is a sectional view of the device in FIG. 1 showing a fluid collector placed before the suction source.

As shown in FIG. 20, a fluid collector 60 may be positioned on the tube 32 between the chamber 22 and the suction device 34. The collector 60 is intended to receive fluid extracted from the chamber space 24 and debris or material from the wound and store such materials for eventual disposal. The collector 60 may be detachable from the tube 32, in order to replace a full collector with an empty collector.

Suction for the wound treatment device is provided by a suction device 34, which may be a pump that is connected and disconnected to the chamber device by appropriate connectors. Although the wound chamber can be used with a motor driven pump, it is also effective with a hand-powered device actuated by the caregiver or patient. The hand-powered device may be a squeeze bulb that provides suction by means of the energy stored in the material of its construction. Alternatively, the suction device may be powered by springs that are compressed by the user. The springs can be selected to produce the clinically desired level of negative pressure. The amount of suction provided by these suction devices is therefore dependent on the level of force generated by squeezed material or the springs. Unlike a motor driven suction pump, the hand powered device preferably cannot produce a high level of suction that may cause an adverse effect to wound healing.

Figure 21:
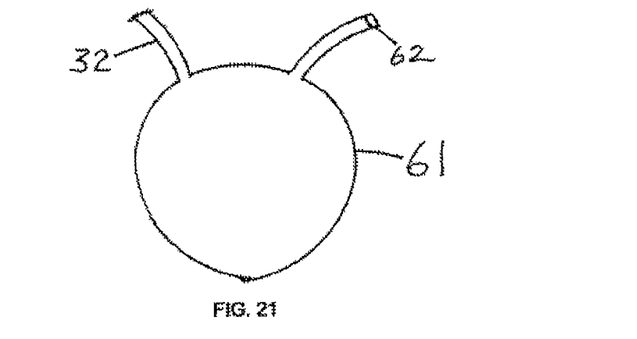
FIG. 21 is a sectional view of a suction device in the form of a squeeze bulb of deformable material.

Referring to FIG. 21, a suction device 61 in the form of a bulb constructed of a deformable material that stores the energy of deformation may be used. The tube 32 communicates with the interior of the suction device 61. A one-way exhaust valve 62 also communicates with the interior of the suction device 61. When the user squeezes the suction device 61, air within the device is expelled through the exhaust valve 62. A portion of the energy used to deform the suction device 61 is stored in the material of which it is constructed, thus maintaining suction within the device, as well as within the tube 32 and the chamber space 24. The bulb is selected and engineered to maintain a constant force and to maintain the clinically desired level of negative pressure within chamber space 24. Fluid from the wound 30 can flow through the tube 32 into the suction device 61 where it can be stored prior to disposal. Once the suction device is full of fluid, the production of negative pressure ceases. The fluid capacity of the suction device thus operates as a safety shut-off mechanism without the need for electronic sensors and controls.

Figure 22:
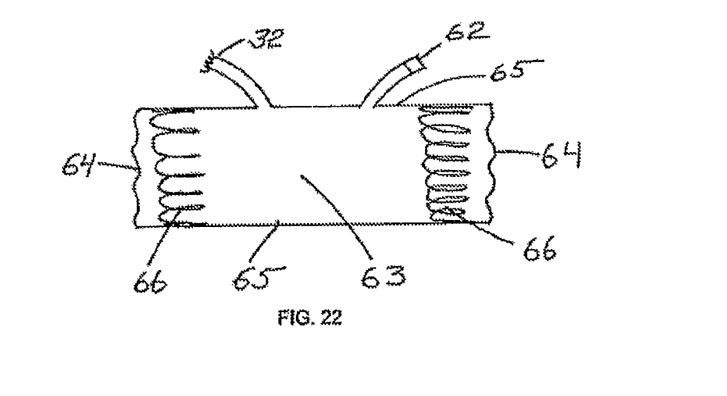
FIG. 22 is a sectional view of a suction device in the form of a flexible chamber containing one or more compression springs.

FIG. 22 shows an alternative suction device 63, consisting of flexible sides 64 and rigid sides 65. Compression springs 66 are located within suction device 63. The tube 32 and the exhaust valve 62 both communicate with the interior of the suction device 63. When the user squeezes the rigid sides 65 towards one another, the springs 66 are compressed and air within the device is expelled through a one-way exhaust valve 62 thus maintaining suction within the device, as well as within the tube 32 and the chamber space 24. The springs 66 are selected and engineered to maintain a constant force against rigid sides 65, and to maintain the clinically desired level of negative pressure within chamber space 24. Fluid from the wound 30 can flow through the tube 32 into the suction device 63 where it can be stored prior to disposal of the entire device 63. This suction device will also cease operating when it is filled with fluid.

Figure 23:
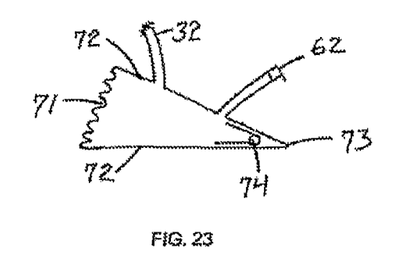
FIG. 23 is a sectional view of a suction device in the form of a wedge-shaped chamber containing one or more torsional springs.
Figure 24:
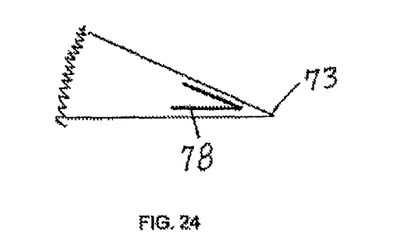
FIG. 24 is a sectional view of the device in FIG. 23 containing a flat spring.

FIG. 23 shows an alternative suction device 70, consisting of rigid sides 72, joined by hinge 73, and flexible side 71. A torsional spring 74 is attached to either the interior or the exterior of rigid sides 72. The tube 32 and the exhaust valve 62 both communicate with the interior of the suction device 70. When the user squeezes the rigid sides 72 towards one another, the spring 74 is compressed and air within the device is expelled through a one-way exhaust valve 62, thus maintaining negative pressure within the device, as well as within the tube 32 and the chamber space 24. The spring 74 is selected and made to maintain a force against rigid sides 72 to maintain the clinically desired level of negative pressure within chamber space 24. Fluid from the wound 30 can flow through the tube 32 into the suction device 70 where it can be stored prior to disposal of the entire device. FIG. 24 shows the device of FIG. 27 where the torsional spring 74 has been replaced by a flat spring 78.

For the previous suction devices, once suction has been established, fluid may flow from the wound to the suction device, where it may be collected and stored for eventual disposal. Alternatively, a separate fluid collector, such as the fluid collector 60 in FIG. 20, can be positioned between the chamber and the suction device. Once the suction device has expanded to its original shape, suction ceases. The suction device will not continue to operate, and can be disconnected and disposed of. If treatment is to be continued, a new suction device can be connected and activated.

Figure 25:
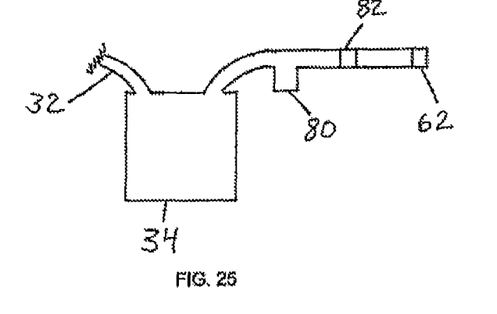
FIG. 25 is a sectional view of a suction device with a trap and filter incorporated into the exhaust port.

FIG. 25 is a sectional view of a trap 80 and a filter 82 interposed between the suction device 34 and the exhaust valve 62 for the purpose of preventing the expulsion of liquids or aerosols from the suction device.

The present invention can be engineered to operate at various levels of negative pressure, in accordance with clinical procedures. Historically, the commonly accepted range of negative pressure is between 0.5 and 2 psi. The device of the present invention operates efficiently in this range. The chamber material conforms to the shape of the wound, and the engineered structures maintain their shape and functionality. However, the chamber can be engineered to operate at higher levels of negative pressure. In addition, if a hand-powered suction device is used, the operating pressure of the device may be higher than the commonly accepted range; that is, the device may operate at a pressure close to 0 psi before suction ceases.

The present invention preferably provides continuous negative pressure, but in practice there may be periods of time when negative pressure is not being produced. In addition, a care giver could provide a program of intermittent negative pressure by manually turning on and off the negative pressure system. Alternatively, the source of negative pressure may be controlled to produce intermittent negative pressure. For example, if a motor-driven pump is provided as the source of negative pressure, the motor may include a controller that is programmed to intermittently provide negative pressure.

The effectiveness of the raised engineered structures in distributing and maintaining negative pressure within the chamber and across the wound surface has been demonstrated in a test model. A wound was created in a sample of animal cadaver tissue. A pressure sensor was installed in the tissue at the center of the wound. A wound chamber device with raised engineered structures on the interior chamber wall was sealed to the skin around the wound. A tube from the chamber device was connected to a source of suction capable of delivering a range of negative pressure. The amount of negative pressure measured at the suction source was compared to the measurement at the center of the wound, in order to determine the effectiveness of the device with respect to the distribution of negative pressure to the wound. The following values were obtained:

| Pressure at Source (mmHg) | Pressure in Wound (mmHg) |
| --- | --- |
| −80 | −65 (81.25% efficiency) |
| −100 | −86 (86.00% efficiency) |
| −120 | −100 (83.33% efficiency) |

The raised engineered structures were observed to maintain their shape with no deformation, thereby preserving their functionality.

The operation of the invention may be illustrated by the following case. A patient with a full-thickness skin wound was treated with a wound chamber negative pressure device connected to a hand-powered suction pump. The interior surface of the chamber contained embossed raised structures. The area around the wound was treated with normal skin disinfectants. The backing from the adhesive base of the chamber was removed, and the chamber was sealed to the normal skin around the wound. The tube was connected to a modified squeeze bulb with an inlet port for fluid, and an exhaust port through which air can be expelled from the bulb. By squeezing the bulb down to its flattest configuration, a negative pressure of 2 psi was established and maintained within the chamber. After the first 24 hours of treatment, the squeeze bulb had expanded to approximately half of its normal size. The bulb was compressed again to its fully flattened configuration. The bulb remained in such configuration for an additional 12 hours, at which point the chamber was removed. The wound showed healthy granulation tissue and progressed to heal rapidly and with minimal scarring. The device produced no adverse effects on the wound or the surrounding skin.

The present invention eliminates many of the drawbacks to existing negative pressure wound therapy systems. For example, the device of the present invention is preferably simplified and lightweight. In some embodiments of the invention, the patient is not restricted to a source of electricity or a battery pack. The system can be worn with ease, so that the patient's mobility is not otherwise compromised. In addition, the wound interface appliance can be applied quickly without the need for custom fitting and construction. The device preferably does not leak due to the smooth adhesive base, eliminating the need for constant suction from an electric pump with sophisticated controls and safety measure. There is no porous wound insert that can potentially cause tissue in-growth and harbor infectious material. Instead, the inner surfaces of the chamber are generally non-porous and non-adherent to prevent any interaction with the wound tissue. Further still, the suction pump preferably has built-in safety limitations on force of suction, duration of operation, and overfilling of the collector for wound fluid.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A device for wound treatment, comprising:
a chamber that includes an inner surface, an outer surface, and a sealing portion that defines an isolated treatment space, the chamber being made of a flexible impermeable material;
a plurality of embossed structures on the inner surface, the embossed structures defining a concave shape relative to the outer surface, the structures configured to directly contact a wound and configured to create pathways through which negative pressure can be distributed and maintained in the isolated treatment space, the plurality of structures intruding from the inner surface of the chamber into the isolated treatment space; wherein all of the pathways for distributing negative pressure are between the inner surface and the wound; and
a tube having a first end connected to the chamber, the tube being in fluid communication with the isolated treatment space so as to enable at least one selected from the group of applying negative pressure to the isolated treatment space and applying a therapeutic modality.

2. The device of claim 1, wherein the plurality of structures are arranged in a pattern to define a channel on the inner surface of the chamber.

3. The device of claim 1, wherein the plurality of structures intrudes into the isolated treatment space in a direction generally perpendicular to the inner surface.

4. The device of claim 1, wherein each embossed structure has a shape selected from the group consisting of a cone, a pyramid, a pentagon, a hexagon, a half sphere, a dome, a rod, an elongated ridge with rounded sides, and an elongated ridge with square sides.

5. The device of claim 1, wherein the chamber comprises a single ply of material.

6. The device of claim 5, wherein each embossed structure is semi-rigid.

7. The device of claim 5, further comprising a base that defines a first opening of the chamber, and wherein the plurality of structures, the chamber, and the base are comprise a single ply of material.

8. The device of claim 1, wherein the chamber has a bellows configuration.

9. The device of claim 1, wherein the sealing portion includes a first surface having an adhesive, and the sealing portion defining a first opening of the chamber.

10. The device of claim 9, wherein the tube connects to the chamber at a position spaced apart from the first opening defined by the chamber.

11. The device of claim 1, further comprising a suction device, a fluid trap, and an exhaust port, wherein the suction device is in fluid communication with the isolated treatment space, the fluid trap, and the exhaust port, and the fluid trap is fluidly positioned between the suction device and the exhaust port.

12. The device of claim 1, further comprising a wedge-shaped manual pump, and wherein the isolated treatment space is in fluid communication with the wedge-shaped manual pump.

13. The device of claim 12, wherein the wedge-shaped manual pump includes a spring that biases the wedge-shaped manual pump to an uncompressed position.

14. The device of claim 1, wherein the chamber is generally cylindrical and configured to treat a wound on a limb.

15. The device of claim 1, wherein the plurality of structures configured for direct contact with the wound are positioned uniformly apart from one another.

16. The device of claim 1, wherein the device is configured to treat the wound for a prolonged duration of a healing process.

17. The device of claim 1, wherein the embossed structures form a projection on the inside surface and a recess on an outside surface.

18. The device of claim 1, wherein the chamber is conformable.

19. The device of claim 1, wherein the plurality of structures configured for direct contact with the wound are positioned non-uniformly apart from one another.

20. A method of treating a wound, comprising:
sealing to a periphery of the wound, a device that defines a treatment space, the device including a chamber having an inner surface, an outer surface, and a tube having a first end connected to the chamber, wherein the tube is in fluid communication with the treatment space so as to enable applying negative pressure to the treatment space, wherein the inner surface includes a plurality of embossed structures that intrude perpendicularly therefrom and define a concave shape relative to the outer surface of the chamber; wherein all of the pathways for distributing negative pressure are between the inner surface and the wound;

evenly applying negative pressure across the wound with the device so that the plurality of embossed structures directly contact the wound and create pathways through which the negative pressure can be distributed and maintained in the treatment space; and maintaining the negative pressure to treat the wound for a significant duration of a healing process.

21. The method of claim 20, the method further comprising the step of applying a therapeutic agent to the wound.

22. The method of claim 20, wherein the device further comprises a suction device for applying the negative pressure, a fluid trap and an exhaust port, wherein the suction device is in fluid communication with the treatment space, the fluid trap and the exhaust port, and wherein the fluid trap is fluidly positioned between the suction device and the exhaust port.

23. The method of claim 20, wherein the device further comprises a wedge-shaped manual pump for applying the negative pressure, and wherein the treatment space is in fluid communication with the wedge-shaped manual pump.

24. The method of claim 23, wherein the wedge-shaped manual pump includes a spring that biases the wedge-shaped manual pump to an uncompressed position.

25. The device of claim 20, wherein the plurality of structures include first structures and second structures, the first structures having a first height dimension and the second structures having a second height dimension, and the first height dimension is greater than the second height dimension.

26. The device of claim 20, wherein each of the embossed structures in the plurality of embossed structures is semi-rigid.

27. The method of claim 20, wherein the plurality of structures that directly contact the wound are positioned uniformly apart from one another.

28. The method of claim 20, wherein applying negative pressure includes conforming the inner surface to the wound.

29. The method of claim 20, wherein the plurality of structures that directly contact the wound are positioned non-uniformly apart from one another.

30. A device for wound treatment, comprising:
a chamber that includes an inner surface and an outer surface and defines a treatment space, the chamber being made of a conformable impermeable material;
a plurality of semi-rigid structures configured to directly contact a wound and configured to create pathways through which negative pressure can be distributed and maintained in the treatment space, the plurality of semi-rigid structures intruding from the inner surface of the chamber into the treatment space and defining a concave shape relative to the outer surface of the chamber; wherein all of the pathways for distributing negative pressure are between the inner surface and the wound; and
a tube having a first end connected to the chamber, the tube being in fluid communication with the treatment space so as to enable at least one selected from the group of applying negative pressure to the treatment space and applying a therapeutic modality,
wherein the device is configured to treat the wound for a prolonged duration of a healing process.

31. The device of claim 30, wherein the chamber is movable over a range of positions, the range of positions including a first position in which the plurality of semi-rigid structures is spaced apart from the first opening of the chamber, and the range of positions further including a second position in which at least some of the plurality of semi-rigid structures is positioned in the first opening of the chamber.

32. The device of claim 30, wherein the plurality of semi-rigid structures covers at least 95 percent of the inner surface.

33. The device of claim 30, wherein the plurality of semi-rigid structures configured to directly contact the wound are positioned uniformly apart from one another.

34. The device of claim 30, wherein the semi-rigid structures are embossed into the chamber.

35. The device of claim 34, wherein the semi-rigid structures define a recess on an outer surface.

36. The device of claim 30, further comprising a base coupled to the chamber and including a sealing portion arranged to seal around a periphery of the wound and isolate the treatment space.

37. The device of claim 36, wherein the sealing portion includes an adhesive.

38. The device of claim 30, wherein the plurality of semi-rigid structures configured to directly contact the wound are positioned non-uniformly apart from one another.

39. A device for wound treatment, comprising:
a wall being made of an impermeable material sufficiently thin to conform to a wound and including an interior surface and an outer surface, the interior surface defining an interior treatment space;
a base coupled to the wall and including an adhesive encompassing the interior treatment space and arranged for sealing engagement with a surface;
a plurality of embossed structures intruding from the interior surface into the interior treatment space and defining a concave shape relative to the outer surface, the structures being configured to directly contact a wound and create pathways through which negative pressure can be distributed and maintained in the interior treatment space; wherein all of the pathways for distributing negative pressure are between the inner surface and the wound; and
a portal supported by the wall and being in fluid communication with the interior treatment space so as to enable at least one selected from the group of applying negative pressure to the treatment space and applying a therapeutic modality.

40. The device of claim 39, wherein the base is disposed apart from the plurality of embossed structures.

41. The device of claim 39, wherein the wall defines a bellows configuration including the plurality of embossed structures.

42. The device of claim 39, wherein the plurality of embossed structures are positioned uniformly apart from one another.

43. The device of claim 39, wherein the wall and the plurality of embossed structures comprise a single ply of material.

44. The device of claim 39, wherein the device is configured to treat the wound for a prolonged duration of a healing process.

45. The device of claim 39, wherein the embossed structures form a projection on the inside surface and a recess on an outside surface.

46. The device of claim 39, wherein the plurality of embossed structures are positioned non-uniformly apart from one another.

47. A device for wound treatment, consisting essentially of:
a chamber that includes an inner surface and an outer surface and a sealing portion that defines an isolated treatment space, the chamber being made of a flexible impermeable material;
a plurality of embossed structures on the inner surface, the structures configured to directly contact a wound and configured to create pathways through which negative pressure can be distributed and maintained in the isolated treatment space, the plurality of structures intruding from the inner surface of the chamber into the isolated treatment space and defining a concave shape relative to the outer surface; wherein all of the pathways for distributing negative pressure are between the inner surface and the wound; and
a tube having a first end connected to the chamber, the tube being in fluid communication with the isolated treatment space so as to enable at least one selected from the group of applying negative pressure to the isolated treatment space and applying a therapeutic modality.

48. A method of treating a wound, comprising:
sealing to a periphery of the wound, a device consisting essentially of a chamber that defines a treatment space, the chamber having an inner surface, an outer surface, and a tube having a first end connected to the chamber, the inner surface including a plurality of embossed structures that intrude perpendicularly therefrom, the embossed structures defining a concave shape relative to the outer surface, wherein the tube is in fluid communication with the treatment space so as to enable applying negative pressure to the treatment space; wherein all of the pathways for distributing negative pressure are between the inner surface and the wound;
evenly applying negative pressure across the wound with the device so that the plurality of embossed structures directly contact the wound and create pathways through which the negative pressure can be distributed and maintained in the treatment space; and
maintaining the negative pressure to treat the wound for a significant duration of a healing process.

49. A device for wound treatment, consisting essentially of:
a wall being made of an impermeable material sufficiently thin to conform to a wound and having an interior surface and an outer surface, the interior surface defining an interior treatment space;
a base coupled to the wall and including an adhesive encompassing the interior treatment space and arranged for sealing engagement with a surface;
a plurality of embossed structures intruding from the interior surface into the interior treatment space and defining a concave shape relative to the outer surface, the structures being configured to directly contact a wound and create pathways through which negative pressure can be distributed and maintained in the interior treatment space; wherein all of the pathways for distributing negative pressure are between the inner surface and the wound; and
a portal supported by the wall and being in fluid communication with the interior treatment space so as to enable at least one selected from the group of applying negative pressure to the treatment space and applying a therapeutic modality.

* * * * *

UNITED STATES PATENT AND TRADEMARK OFFICE
CERTIFICATE OF CORRECTION

| | | |
|---|---|---|
| PATENT NO. | : 8,632,523 B2 | Page 1 of 1 |
| APPLICATION NO. | : 12/601394 | |
| DATED | : January 21, 2014 | |
| INVENTOR(S) | : Eriksson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this
Twenty-first Day of July, 2015

Michelle K. Lee
*Director of the United States Patent and Trademark Office*